(12) United States Patent
Ottma

(10) Patent No.: US 9,597,088 B2
(45) Date of Patent: Mar. 21, 2017

(54) MEDICAL IMPLANT AND MANUFACTURING METHOD THEREOF

(71) Applicant: Occlutech Holding AG, Schaffhausen (CH)

(72) Inventor: Rüdiger Ottma, Großschwabhausen (DE)

(73) Assignee: Occlutech Holding AG, Schaffhausen (CH)

( * ) Notice: Subject to any disclaimer, the term of this patent is extended or adjusted under 35 U.S.C. 154(b) by 0 days.

(21) Appl. No.: 15/073,384

(22) Filed: Mar. 17, 2016

(65) Prior Publication Data

US 2016/0192943 A1 Jul. 7, 2016

Related U.S. Application Data

(63) Continuation of application No. 13/698,978, filed as application No. PCT/EP2011/058381 on May 23, 2011, now Pat. No. 9,295,472.
(Continued)

(30) Foreign Application Priority Data

May 23, 2010 (EP) .................................. 10163679

(51) Int. Cl.
*A61M 29/00* (2006.01)
*A61B 17/12* (2006.01)
*A61B 17/00* (2006.01)

(52) U.S. Cl.
CPC .... *A61B 17/12172* (2013.01); *A61B 17/0057* (2013.01); *A61B 17/12109* (2013.01);
(Continued)

(58) Field of Classification Search
CPC ...... A61B 17/1022; A61B 17/1266–17/12177; A61B 17/1214;
(Continued)

(56) References Cited

U.S. PATENT DOCUMENTS 5,725,552 A 3/1998 Kotula et al.
5,846,261 A * 12/1998 Kotula ............... A61B 17/0057
606/213
(Continued)

FOREIGN PATENT DOCUMENTS

EP 2014240 A1 1/2009
WO WO96/01599 A1 1/1996
WO WO2009/016265 A2 2/2009

OTHER PUBLICATIONS

United States Patent and Trademark Office, Notice of Allowance mailed Nov. 24, 2015 in U.S. Appl. No. 13/698,978, 8 pages.
(Continued)

*Primary Examiner* — Melanie Tyson
*Assistant Examiner* — Erich Herbermann
(74) *Attorney, Agent, or Firm* — Inskeep IP Group, Inc.

(57) ABSTRACT

A medical implantable occlusion device (100) is disclosed comprising a braiding of at least one thread, an expanded diameter portion (102), and a tubular member (103) having a distal endpoint closest to the expanded diameter portion having a distal rim (107). The braiding comprises a stem (108) having a first end connected to the expanded diameter portion and a second end connected to the distal region, where the stem in a relaxed state is partly sunk into the tubular member beneath the distal rim (107), wherein the proximal region comprises a connecting member (113), wherein ends of the at least one thread are fixed to the connecting member, the expanded diameter portion comprises returning loops of the at least one thread whereby opposite ends of the at least one thread forming the expanded diameter portion are fixed to the connecting member.

19 Claims, 4 Drawing Sheets

Related U.S. Application Data

(60) Provisional application No. 61/347,463, filed on May 24, 2010.

(52) U.S. Cl.
CPC ............ *A61B 2017/00526* (2013.01); *A61B 2017/00575* (2013.01); *A61B 2017/00592* (2013.01); *A61B 2017/00606* (2013.01); *A61B 2017/00628* (2013.01); *A61B 2017/00867* (2013.01); *Y10T 29/49826* (2015.01)

(58) Field of Classification Search
CPC .......... A61B 17/0057; A61B 17/12122; A61B 17/12027; A61B 17/1203; A61B 17/12099; A61B 17/12104; A61B 17/12109; A61B 17/12113; A61B 17/12145; A61B 17/1215; A61B 2017/00526; A61B 2017/00575; A61B 2017/00579; A61B 2017/00592; A61B 2017/00597; A61B 2017/00606; A61B 2017/00601; A61B 2017/00628; A61B 2017/00637; A61B 2017/00659
USPC ............... 606/191, 200, 213–215; 623/23.72
See application file for complete search history.

(56) References Cited

U.S. PATENT DOCUMENTS

| | | |
|---|---|---|
| 2007/0004339 A1 | 1/2007 | Lin et al. |
| 2007/0043391 A1 | 2/2007 | Moszner et al. |
| 2007/0112380 A1 | 5/2007 | Figulla et al. |
| 2008/0262518 A1* | 10/2008 | Freudenthal ....... A61B 17/0057 606/151 |
| 2009/0018562 A1 | 1/2009 | Amplatz et al. |
| 2009/0099647 A1 | 4/2009 | Glimsdale et al. |
| 2009/0306706 A1* | 12/2009 | Osypka .............. A61B 17/0057 606/213 |
| 2010/0023048 A1 | 1/2010 | Mach |

OTHER PUBLICATIONS

United States Patent and Trademark Office, Office Action mailed Jun. 4, 2015 in U.S. Appl. No. 13/698,978, 11 pages.
WIPO, European International Preliminary Examining Authority, International Preliminary Report on Patentability mailed Oct. 1, 2012 in International Patent Application No. PCT/EP2011/058381, 10 pages.
WIPO, European International Search Authority, International Search Report mailed Sep. 22, 2011 in International Patent Application No. PCT/EP2011/058381, 6 pages.

* cited by examiner

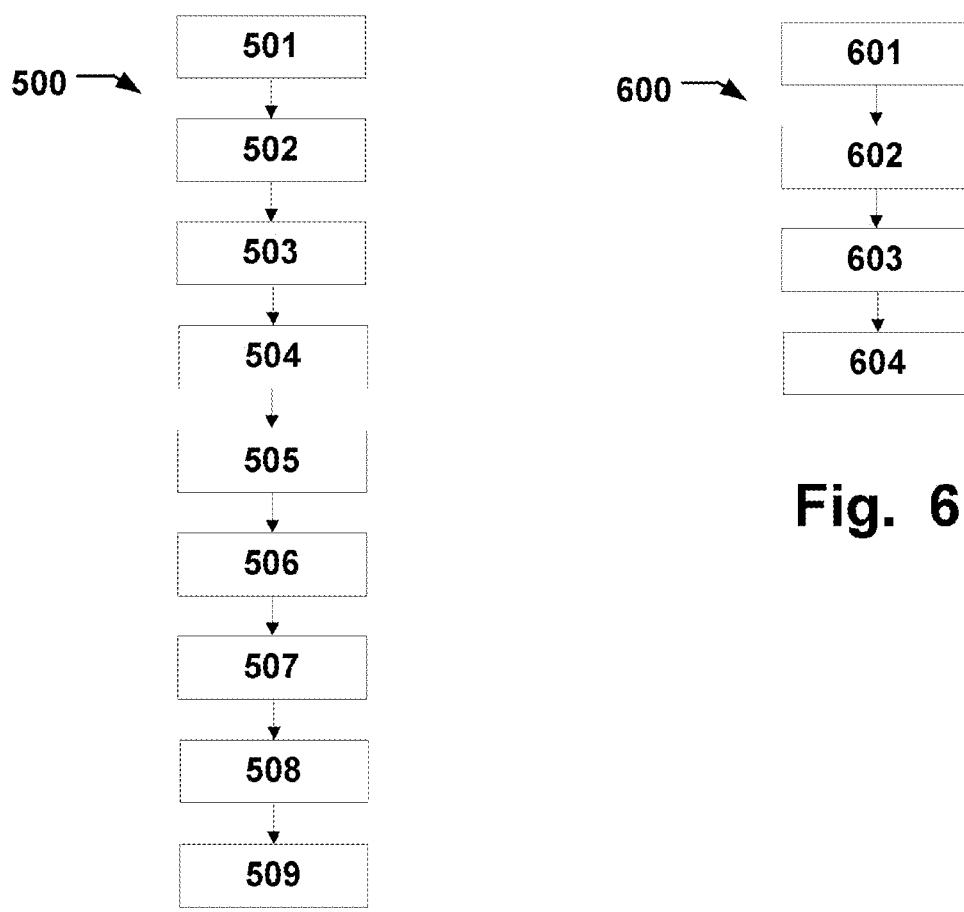

MEDICAL IMPLANT AND MANUFACTURING METHOD THEREOF

RELATED APPLICATIONS

This application claims priority to U.S. patent application Ser. No. 13/698,978 filed Jun. 4, 2013 entitled Medical Implant And Manufacturing Method Thereof, which is the U.S. National Phase of and claims priority to International Patent Application No. PCT/EP2011/058381, International Filing Date May 23, 2011, entitled Medical Implant And Manufacturing Method Thereof, which claims benefit of European Application No. 10163679.3, filed May 23, 2010 entitled Medical Implant And Manufacturing Method Thereof, and U.S. Provisional Application Ser. No. 61/347,463, filed May 24, 2010 entitled Medical Implant And Manufacturing Method Thereof, all of which are incorporated herein by reference in their entireties.

FIELD OF THE INVENTION

This invention pertains in general to the field of medical implants, as well as methods for manufacturing such implants. More particularly the invention relates to an intraluminally deliverable occlusion device for selective occlusion of a target site in a body lumen, such as the body's circulatory system.

BACKGROUND OF THE INVENTION

Various intravascular deliverable devices are used for treating specific conditions via access through body lumina, such as patients circulatory system. The target site may for instance be an atrial or ventricular septum having a defective opening to be occluded, such as devices for treating septal defects and the like. In certain circumstances, it may be necessary to occlude a patient's lumen, vessel, chamber, channel, hole, or cavity such as to stop blood flow there through. One such condition known in the art is a patent ductus arteriosus (PDA), which is essentially a condition wherein two blood vessels, most commonly the aorta and pulmonary artery adjacent the heart, have a blood flow shunt between their lumens. Blood can flow directly between these two blood vessels through the passageway, compromising the normal flow of blood through the patient's vessels. Other physiologic conditions in the body occur where it is also desirous to occlude a vessel, a shunt between vessels, or an ostium at a branch vessel, in order to prevent blood flow through the vessel.

An occlusion device for treatment of such heart disease is disclosed in United States patent application publication number 2009/0187214. A tubular member of a braided fabric is disclosed having disc-shaped portions connected to either side of the tubular member via transition segments having reduced cross-sectional dimension. The device is delivered by a catheter connected to either of the discs. The discs engage with the walls of the septum. The diameter and length of the PDA is determined by angiography in order to select the size of the device, where the latter dimension requirement is a particular issue due to the double disc design, which furthermore is increasing the complexity of the device and the delivery thereof.

EP2014240 discloses a medical device having a cylindrical body portion, a disc portion, and a small transition diameter there between. The transition diameter is recessed within an indention. A problem with the device is lack of flexibility and compactness of the device.

A problem with prior art is to achieve sufficient flexibility while maintaining a compact device. This applies in particular during delivery through tortuous channels. Flexibility is also desired during deliver when releasing the implantable device out of a catheter to the target site. Moreover, a degree of flexibility to accommodate anatomical movements without fatigue or risk of loosening from the implantation site during an ingrowth period is also a desired characteristic of such devices. Further, a compact device is desirable for quick and easy delivery, for example via a catheter, and for occupying less space in the body, thereby reducing chance of interference with bodily functions. A more flexible implant is desired in terms of adjustments of the device used and applied methods, due to the fact that different patients are anatomically slightly different to one another and that the deficiency to be treated is most often individual and unique for each patient treated.

A problem with prior art is to achieve a secure attachment of the device in the body while maintaining ease of delivery. Secure attachment is necessary for patient safety and achieving the intended treatment of the septal defect.

Thus, there is a need for an implant which adjusts for differences in the cardiovascular system between patients still allowing a secure deployment of a medical implant.

Also, a problem with prior art is that delivery of the device via the aorta having a high pressurized blood environment may give rise to several undesired conditions. Debris, e.g. from arteriosclerotic deposits scraped loose by the device under delivery, for instance at ostia of branch vessels, may cause embolic complications. Embolic material could thus be transported to vital organs, e.g. to the brain via the subclavian vessels, and cause blood clots, leading to stroke.

The above problems may have dire consequences for the patient and the health care system. Patient risk is increased.

Hence, an improved implant would be advantageous and in particular allowing for increased flexibility, cost-effectiveness, and/or patient safety would be advantageous. Also, and a method for manufacturing such medical implant would be advantageous.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a device and a method according to the appended patent claims.

Embodiments of the present invention may be well suited for the selective occlusion of a vessel, lumen, channel, hole, cavity, or the like. One particular example, without limitation, of such a condition is a Patent Ductus Arteriosus (hereinafter PDA). Another example is a vessel, lumen, channel, hole or shunt, through which blood flows from one vessel to another vessel such as an Atrial Septal Defect (herein after ASD) or a Ventricular Septal Defect (herein after VSD). Other examples could be an Arterial Venous Fistula (AVF), Arterial Venous Malformation (AVM), a Patent Foramen Ovale (PFO), or a Para-Valvular Leak (PVL).

According to a first aspect of the invention a medical implantable occlusion device is provided comprising a braiding of at least one thread, where the braiding has an unloaded relaxed state and a stretched state. The braiding comprises an expanded diameter portion, and a tubular member extending along a longitudinal axis. The tubular member has a distal region towards the expanded diameter portion and an opposite proximal region, where a distal endpoint of the distal region closest to the expanded diameter portion has a distal rim in a plane substantially orthogonal to the longitudinal axis. The braiding comprises a stem having a first end connected to the expanded diameter portion and a second end connected to the distal region, where the stem in the relaxed state is partly sunk into the tubular member beneath the distal rim whereby the second end of the stem is displaced from the distal rim by a first offset along the longitudinal axis. The proximal region comprises a connecting member for a delivery device, wherein ends of the at least one thread are fixed to the connecting member, and wherein the expanded diameter portion comprises returning loops of the at least one thread whereby opposite ends of the at least one thread forming the expanded diameter portion are fixed to the connecting member.

According to a second aspect of the invention a method of manufacturing a medical implantable occlusion device of a braiding of at least one thread is provided. The method comprises forming the braiding in a first heat setting step to a first intermediate shape comprising a tubular member and an expanded diameter portion, attaching a secondary tool to the braiding having the first shape, and forming the braiding in a second heat setting step to a second shape by the secondary tool, where the braiding partly maintains the first shape.

Further embodiments of the invention are defined in the dependent claims, wherein features for the second and subsequent aspects of the invention are as for the first aspect mutatis mutandis.

Some embodiments of the invention provide for flexible positioning of a medical implant to varying anatomical sites in a body of a human or animal.

Some embodiments of the invention also provide for secure attachment of a medical implant in a patient's vascular system.

Some embodiments of the invention provide for a compact medical implant with maintained flexibility.

Some embodiments of the invention provide for a medical implant that can be safely delivered to a treatment site in a patient.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 5 is a flow chart illustrating a method of manufacturing of a medical implantable occlusion device according to an embodiment of the invention; and FIG. 6 is a flow chart illustrating a method of occluding a shunt in a body lumen with a medical implantable occlusion device according to an embodiment of the invention.

DESCRIPTION OF EMBODIMENTS

Figure 1:
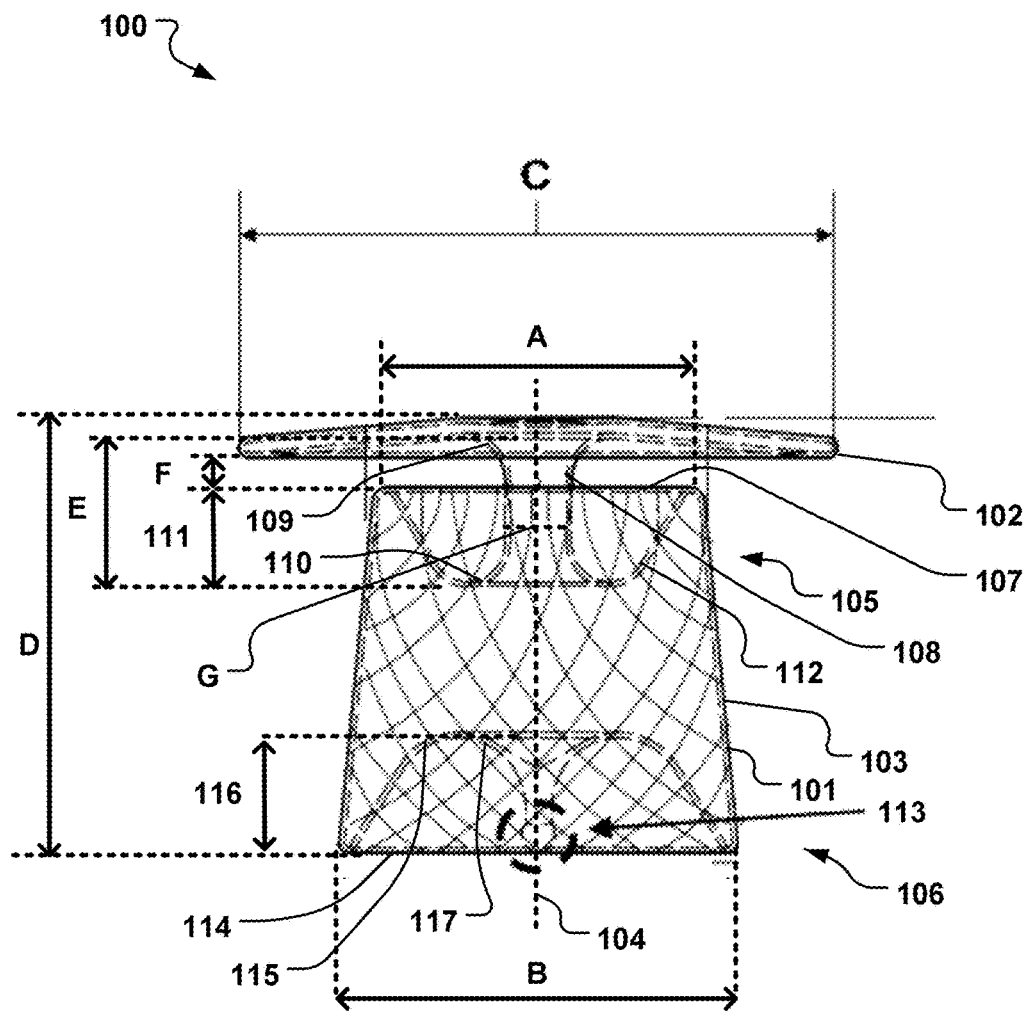
FIG. 1 is an illustration of a medical implantable occlusion device according to an embodiment of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to a PDA plug. However, it will be appreciated that the invention is not limited to this application but may be applied to many other medical implantable devices, including for example filters, stents, Left Atrial Appendage (LAA) occluders, aneurysm treatment devices, grafts, etc.

FIG. 1 shows a medical implantable occlusion device 100 according to an embodiment of the invention. The device 100 comprises a mesh or braiding 101 of at least one thread. The braiding 101 may be formed from one thread or several. The device 100, or more particularly the braiding 101, has an unloaded relaxed state and a stretched state. Thus, in the relaxed state, wherein the device 100 has a shape as depicted in FIG. 1, no external force acts on the device 100. The device 100 may be stretched and thereby exhibit a smaller cross-section, in order to fit inside a delivery device such as a catheter. The device 100 may be self-expandable between the stretched state and the relaxed state, i.e. when the device 100 is removed from the confinement of the catheter the cross-section of the device 100 returns to its originally defined value in the unloaded relaxed state. The device may be self-expandable due to an inherent elasticity of the threads in the braiding. The device may also have a shape memory, e.g. triggerable to go to the relaxed state at a switching temperature, such as body temperature. Alternatively, or in addition, in other embodiments of the implantable device, expansion devices (not shown), such as inflatable balloons, may be used to bring the device from the collapsed state to the expanded, relaxed state.

The shape of the device 100 in the relaxed state may be defined in a heat treatment procedure of the device 100 or more particularly of the braiding 101. The dimensions of the device 100 in the relaxed state are defined in the heat treatment procedure if the braiding. A particular embodiment of the manufacturing method is described below.

The entire device 100 may be comprised of a single, continuous braiding 101. The braiding 101 may be made of a material suitable for implanting in a human or animal body, and suitable for being formed in a heat treatment procedure to a desired shape in the unloaded relaxed state and also in the stretched state. For example NiTinol may be used as a material for the device 100. However, suitable materials for embodiments of the braiding are various and include shape memory materials, metal, superelastic alloys (such as NiTinol), or polymers, such as degradable polymers.

The braiding 101 comprises an expanded diameter portion 102, and a tubular member 103 extending along a longitudinal axis 104. The tubular member 103 has a distal region 105 towards the expanded diameter portion 102 and an opposite proximal region 106. The distal region 105 comprises a distal rim 107 corresponding to the distal endpoint of the distal region 105 closest to the expanded diameter portion 102. The distal rim 107 corresponds to the edge of the tubular member 103 that faces the expanded diameter portion 102, and is aligned in a plane substantially orthogonal to the longitudinal axis 104.

The braiding 101 comprises a stem 108 having a first end 109 connected to the expanded diameter portion 102 and a second end 110 connected to the distal region 105 of the tubular member 103. In the unloaded relaxed state of the device 101 as shown in FIG. 1 the stem 108 is partly sunk into the tubular member 103 beneath the distal rim 107. Thus, the second end 110 of the stem 108 is displaced from the distal rim 107 by a first offset 111 along the longitudinal axis 104.

The displacement of the stem 108 into the tubular member 103 provides a more compact device 100. As the length (E) of the stem 108 is maintained while the device 100 is more compact, i.e. due to decreased length (D), the function of the stem 108 for providing flexibility between the tubular member 103 and the expanded diameter portion 102 is maintained.

By stretching the device 100, e.g. by moving the expanded diameter portion 102 and the tubular member 103 in opposite directions along the longitudinal axis 104, the device 100 is put in the stretched state and the first offset 111 may decrease. As the stem 108 is partially sunk into the tubular member 103 the amount of displacement possible of the device 100 from the unloaded relaxed state, e.g. by aforementioned stretching, could be increase as the stem 108 may be stretched out of the tubular member 103, for example by an amount corresponding to the offset 111 of the device in the relaxed state. Various offsets 111 may be defined for the device 100 in the relaxed state.

Alternatively, or in addition, the length of the stem 108 may substantially remain constant without being stretched. This allows for a particular stable long-term construction even in anatomical situations where a continuous movement at the implantation site is present. The stem may be made of a portion of parallel threads or a more densely braided section of the braiding 101 at the stem 108, providing for particular strength in the longitudinal direction.

The distal region 105 has a curved braiding having an apex at the second end 110 of the stem and a distal surface 112. This may provide an inherent flexibility in use, drawing the tubular part 103 and the expanded diameter part 102 longitudinally towards each other. The shape and spatial extent of the distal surface 112 provides a spring like portion. This spring-like portion is shown left and right to the diameter G in FIG. 1. This provides for advantageously controllable self-contraction properties of the device 100. As substantially the entire distal surface 112 enclosed by the distal rim 107 is recessed, as seen in FIG. 1, the range of motion and flexibility or spring-like action is improved, as discussed further below. I.e. the diameter of the recessed distal surface 112 may be substantially equal to the diameter of the distal rim 107. Also the distal surface 112 may be substantially concave towards the expanded diameter portion 102, as seen in FIG. 1, and/or having a portion close to the second end 110 extending radially substantially parallel to the expanded diameter portion 102. This further allows for increased flexibility of the stem 108 and expanded portion 102 as the area of the flexible recessed surface 112 is increased, as the amount of material being flexible is increased, without increasing the dimensions of the device 100 externally.

As the device 100 may strive towards the relaxed state by being self-expandable, or rather self-contracting, between the stretched state and the relaxed state, an inherent force may act on the stem 108 to maintain the offset 111 as defined in the relaxed state. By removing the external forces on the device 100 and thereby release it from the stretched state, the braiding 101 may return to its original shape in the relaxed state due to the aforementioned inherent force. The original shape of the device 100 may be defined in a heat treatment procedure in a manufacturing step. The inherent force pulls the expanded diameter portion 102 towards the tubular member 103 as soon the stem 108 is displaced from the shape of the device 100 in the relaxed state. As the stem 108 is partially sunk into the tubular member 103 a large flexibility is obtained as the device 100 may be stretched by expansion of the stem 108 from the tubular member 103 with reduction of the offset 111 from its defined value in the relaxed state while the inherent force act to contract the expanded diameter portion 102 towards the tubular member 103. This is advantageous as a single device 100 can be applied to occlude various PDA with different lengths while maintaining secure attachment of the device 100 at the PDA as the diameter portion 102 will be contracted towards the tubular member 103 for each length configuration possible for the device 100, i.e. for each displacement of the stem 108 relative to the distal rim 107.

The tubular member 103 may comprise biocompatible fibres or patches of for example of PET that support sealing of the blood flow through the device 100, and thereby the shunt to be occluded.

The tubular member 103 may be tapered towards the expanded diameter portion 102. The diameter (B) of the endpoint of the proximal region 106 is thereby larger than the diameter (A) of the endpoint of the distal region 105. When positioned in the PDA the tapered shape towards the expanded diameter portion 102 create an increased force acting on the walls of the PDA to be occluded as the expanded diameter portion 102 is pulled towards the tubular member 102 by the aforementioned inherent force if the device 100 is self-contracting. The proximal region 106 will exert a compressive force towards the expanded diameter portion 102 by the tapered configuration in comparison to a pure frictional force in case the device is not tapered, or tapered in the other direction. The tapered shape, similar to a champagne cork, has a function similar to an oversized cork at one end, leading to improved retention in body lumina. This is in particular advantageous with shunts that anatomically have an increasing lumen diameter in the same direction as the tapering and where the expanded diameter portion provides further increases locking of the device in the shunt. In particular the expanded diameter portion is substantially flat and has a diameter larger than an ostium of the shunt into which it is placed. Thus the rim of the periphery of the expanded diameter portion may advantageously engage the tissue around the ostium. The closure effect is further improved when a higher pressure is applied from the distal side towards the distal end of the device, such as when the device 100 is arranged in a PDA. Here, the tubular portion is arranged in the shunt channel of the PDA and the expanded diameter portion is arranged in the aortic arch around the ostium of the PDA. Thus a secure occlusion is achieved even before the device is securely covered with endothelia and tissue integrated with the surrounding tissue.

The distance (F) between the distal rim 107 and the expanded diameter portion 102 may be substantially smaller than the length of the stem 108. By increasing the offset 111 in relation to the distance (F) a more compact device 100 may be obtained while maintaining the flexibility discussed above. The distance (F) may be increased so that the expanded diameter portion 102 and the stem 108 may pivot more from side to side without the expanded diameter portion 102 interfering with the distal rim 107.

The stem 108 may be pivotable with respect to the tubular member 103 around the second end 110 of the stem 108. In this way the angle of the expanded diameter portion 102 in relation to the tubular member 103 may be changed depending on the anatomy of the site in the vascular system to be occluded. The length (F) of the stem 108, and the amount of offset 111 and distance (F) may affect the amount the stem 108 may be pivoted and thereby the amount of angular displacement of the expanded diameter portion 102.

The stem 108 may be concentric with respect to the tubular member 103. A symmetric shape of the device 100 may increase the flexibility of the expanded diameter portion 102 in relation to the tubular member 103. An asymmetric configuration may be suitable in particular anatomies to be occluded.

In FIG. 1 the second end 110 of the stem 108 is connected to the distal surface 112 of the distal region 105. The distal surface 112 is sunk into the tubular member 103 beneath the distal rim 107. As the second end 110 of the stem 108 is connected to the distal surface 112 which is sunk into the tubular member 103 beneath the distal rim 107 the flexibility of the stem 108 in relation to the tubular member 103 may be increased. The entire distal surface 112 may be flexible to allow movement of the stem 108 in relation to the tubular member 103. The stem 108 may be flexible by itself as the braiding 101 forming the stem 108 may provide for flexibility. Alternatively, or in addition, the stem 108 may be of a flexible material. Tilting of the distal surface 110 in relation to the longitudinal axis 104 may provide for increased angular displacement of the expanded diameter portion 102 in relation to the tubular member 103.

The distal surface 112 may be confined to a region of the braiding 101 between the stem 108 and the distal rim 107. The diameter of the distal surface 112 may be substantially equal to the diameter of the distal rim 107, i.e. substantially equal to the diameter (A) in FIG. 1. Hence, the surface of the braiding 101 inside the distal ring 107 is sunk into the tubular member 103. As a larger portion of the surface of the braiding between the second end 110 of the stem 108 and the distal rim 107 is sunk into the tubular member 103 an increased range of motion may be possible for the stem 108, and thereby an increased flexibility of the expanded diameter portion 102. This is in contrast to cases where only a minor part of the distal surface is recessed, which could not provide the same range of motion of the distal surface 112 and thereby not the same range of motion of the expanded diameter portion 102. Hence, in such cases, the device will not be able to conform to such wide range of anatomies as the device 100 of the current invention.

The expanded diameter portion 102 may be a disc shaped portion. The disc may be bent with its outer periphery closer towards the tubular portion than the center portion thereof. Alternatively, it may have any shape suitable for the particular anatomy of the site to be occluded.

The outer diameter (C) of the expanded diameter portion 102 may be substantially larger than a diameter of the tubular member 103, as depicted in FIG. 1. An increased diameter (C) may reduce the pressure exerted by the expanded diameter portion 102 on the vessel wall at the occlusion site, and decrease the risk of the device 100 being dislodged from the occlusion site. The diameter may be equivalent to the largest cross-section throughout the disclosure.

The diameter (G) of the stem 108 may be substantially smaller than any diameter of the tubular member (A, B). A smaller diameter may increase the flexibility of the expanded diameter portion 102.

The proximal portion 102 may comprise a connecting member 113 for a delivery device (not shown). The delivery device may grasp the connection member 113 which may be spherical in shape, thus providing a pivoting motion of the device 100 in relation to the delivery device in combination with secure attachment. The ends of the at least one thread forming the braiding 101 may be fixed to the connecting member 113. The connecting member 113 may thus be a weld or any other attachment means for the threads of the braiding 101. The connecting member may comprise a threaded screw attachment (not shown) of female or male type for threaded attachment to a delivery device having corresponding threads. The expanded diameter portion 102 may comprise returning loops of the at least one thread, meaning that opposite ends of the at least one thread forming the expanded diameter portion 102 are fixed to the connecting member 113. By having returning loops only one collection point for the ends of the at least one thread is needed. The connection member 113 may thus serve as a connection for these ends, thereby avoiding multiple connection points such as welds on the expanded diameter portion 102. Hence, a flat expanded diameter portion 102 may be provided, that increases the compactness of the device 100. Thereby no parts of the device 100 extend beyond the expanded diameter portion. By having such compact device 100, it may be easily positioned and manipulated at the target site. This is in contrast to cases having protruding parts at both the distal and proximal ends, which could not attain the same degree of compactness of the device. Further, due to the connection member 113 on the proximal end 106, the device 100 may be delivered through the vena cava with improved safety to the patient. Delivery to the high pressure arterial side of the vascular system is avoided, which provides for less complications and a medical procedure which is simpler to perform.

Similarly to the distal region 105 of the device 100 the proximal region 106 may have a proximal rim 114 and a proximal surface 115. A distal end 117 of the connection member 113 may have a second offset 116 in relation to the proximal rim 114.

The proximal surface 115 may be confined to a region of the braiding 101 between the connecting member 113 and the proximal rim 114. The diameter of the proximal surface 115 may be substantially equal to the diameter of the proximal rim 114, i.e. substantially equal to the diameter (B) in FIG. 1. Hence, the surface of the braiding 101 inside the proximal ring 114 is sunk into the tubular member 103. This may provide increased flexibility of the connecting member 113 in relation to the tubular member 103, and also the device 100 becomes more compact, as the entire length of the connecting member 108 may be sunk into the tubular member 103. Alternatively, in other embodiments, the connecting member 113 may protrude proximally of the tubular portion.

Figure 2:
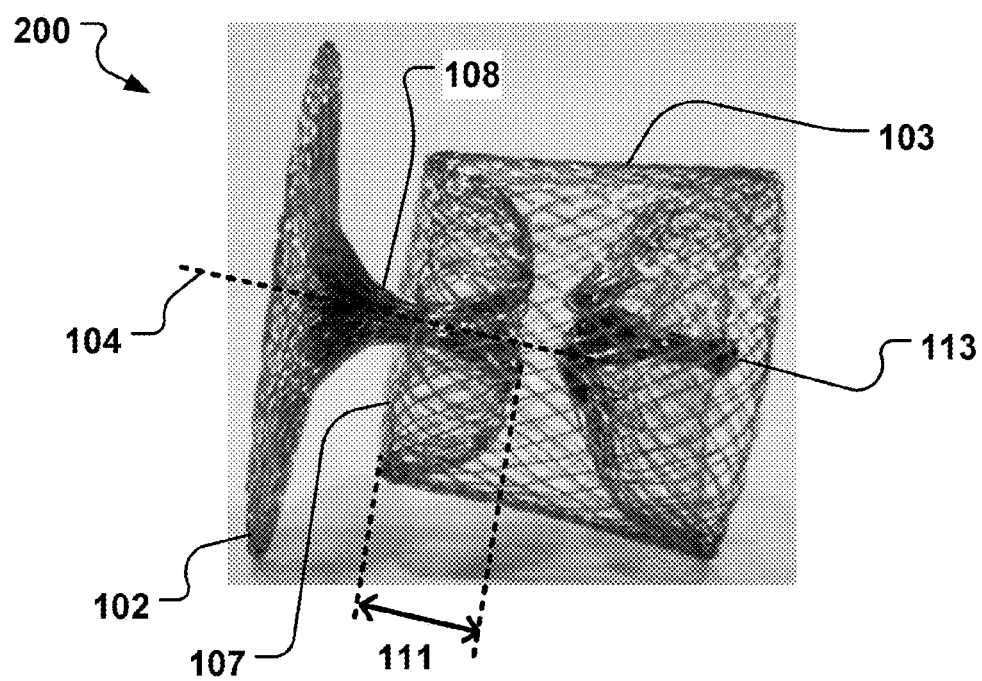
FIG. 2 is an illustration of a medical implantable occlusion device according to an embodiment of the invention.

FIG. 2 shows a perspective view of a medical implantable occlusion device 200 according to an embodiment of the invention. The stem 108 of the device 200 has an offset 111 from the distal rim 107 into the tubular member 103, providing the advantages as described above. A connecting member 113 in the form of a spherical ball is provided at the proximal end for connecting to a mating socket.

Figure 3:
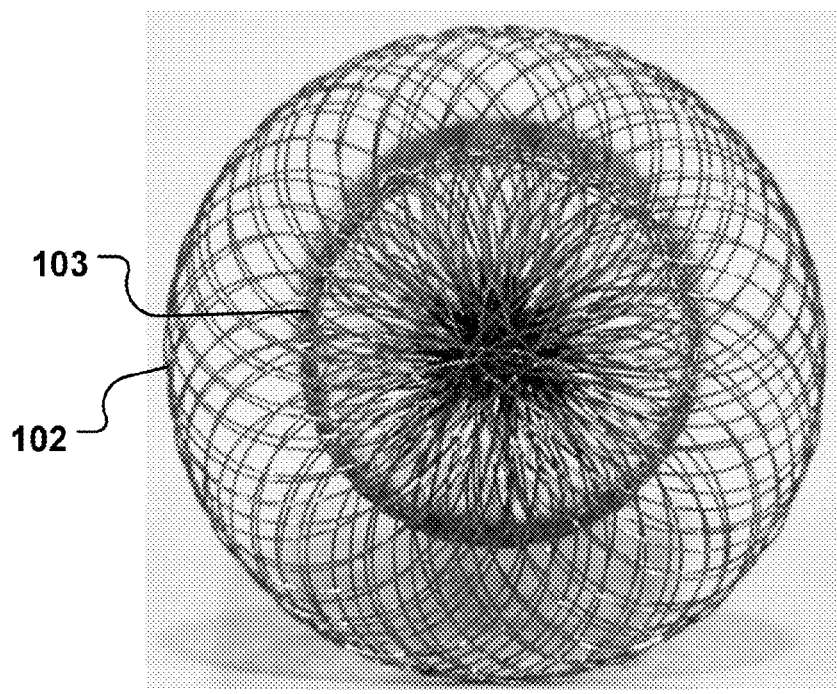
FIG. 3 is a side view the medical implantable occlusion device in FIG. 2.

FIG. 3 shows a side view of the device 200 in FIG. 1. The expanded diameter portion 102 is disc-shaped and is substantially concentrically aligned with the tubular member 103.

FIG. 4 and FIG. 5 illustrate a method 500 of manufacturing a medical implantable occlusion device 100, 200, of a braiding 101 of at least one thread. The method comprises forming 501 the braiding 101 in a first heat setting step to a first shape 405 comprising a tubular member 103 and an expanded diameter portion 102. A secondary tool 401 is attached 504 to the braiding 101 having the first shape 405. The braiding 101 is in the following formed 506 in a second heat setting step to a second shape 406 by the secondary tool 401, as shown in FIGS. 4b-c. The braiding 101 maintains partly the first shape 405.

The method 500 comprises further welding 503 a bundle of threads of the braiding 101 at a proximal end 106 of the tubular member 103 after forming the first shape 405. Alternatively, the welding may be performed after any manufacturing step. The method 500 comprises annealing 502, 509, the braiding 101 in the heat setting steps after forming each of the first and second shapes 405, 406, respectively. By annealing the braiding 101 the desired shapes 405, 406, can be maintained.

Figure 4A:
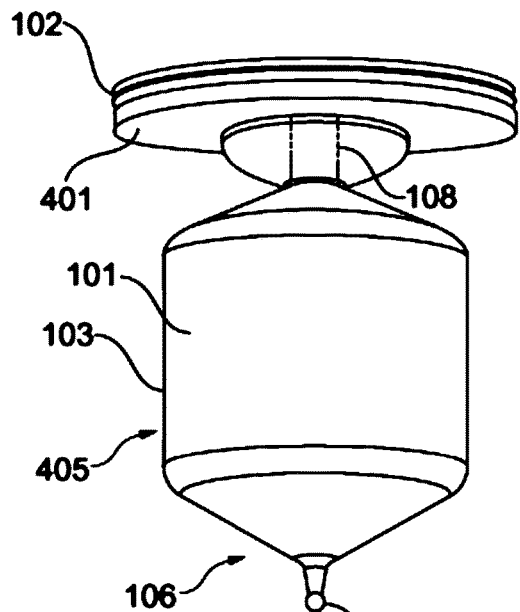
FIGS. 4a-d are illustrations of a medical implantable occlusion device according to an embodiment of the invention during a manufacturing step.
Figure 4B:
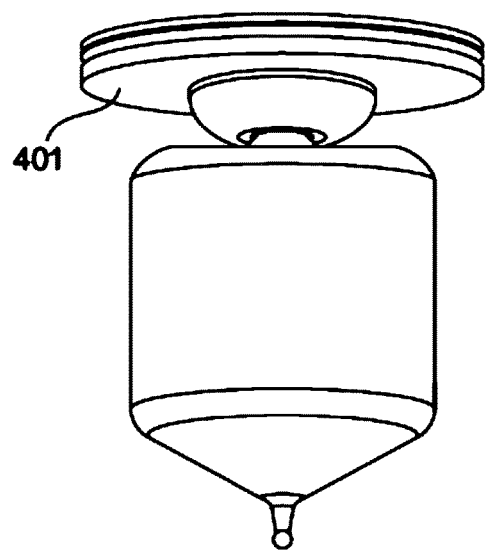

When forming the second shape 406 the method 500 comprises moving 507 the secondary tool 401 into the braiding 101 to produce at least one recess 402 into the tubular member 103. In FIG. 4b the secondary tool 401 is partly moved towards tubular member 103, and in FIG. 4c the secondary tool 401 is sunk into the tubular member 103 creating a recess 402. Similarly, a secondary tool may be sunk into the proximal region such that the connecting member 113 is sunk into the tubular body 103.

Figure 4C:
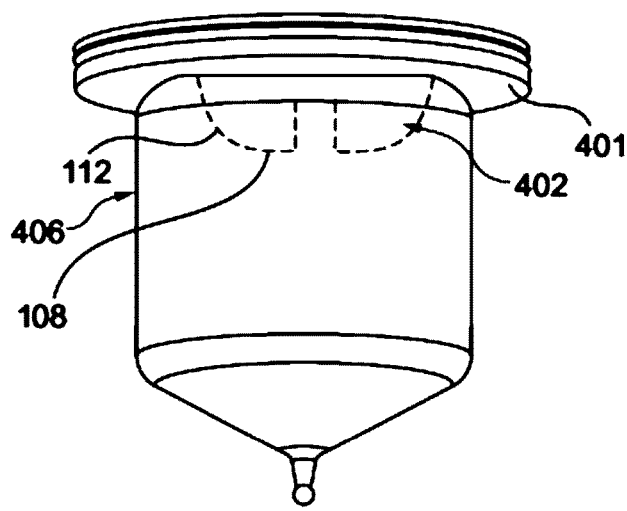
Figure 4D:
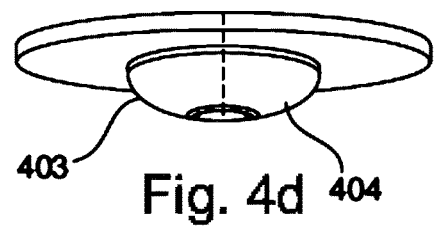

In forming the second shape 406 the method 500 comprises attaching 505 the secondary tool around the stem 108 of the braiding 101. The stem 108 is between and connects the tubular member 103 and the expanded diameter portion 102. When moving 508 the secondary tool 401 into the tubular member the stem 108 is partly sunk into the tubular member 103 as illustrated in FIG. 4c. The braiding 101 in the second shape 406 with the stem 108 recessed into the tubular member 103 may then be annealed and the secondary tool 401 may be removed. The second shape 406 may then correspond to the unloaded relaxed state of the braiding 101 of the device 100, 200. In other embodiments the secondary tool 401 may be attached to the braiding 101 at any location between the proximal region 106 and the opposite end point of the device 100, 200, such as the expanded diameter portion 102, for forming the device 100, 200, into a second shape 406 that may be integral with the first shape 405, e.g. the first and second shapes 405, 406 may define the outside and inside contours of the device 100,200, respectively.

The secondary tool may comprise at least two connectable portions 403, 404 for attachment around the stem 108 of the braiding 108.

FIG. 6 illustrates a medical method 600 of occluding a shunt in a body lumen, comprising providing 601 a device 100, 200, inserting 602 the device 100, 200 in a collapsed state into the shunt, expanding 603 and releasing the device 100, 200, in the shunt, thus anchoring 604 the device 100, 200, in the shunt for occluding the latter by the device 100, 200.

The device is that of the first aspect of the invention. Particularly advantageous anchoring and occlusion may be achieved while maintaining the aforementioned flexibility of the device. The shunt is for instance a Patent Ductus Arteriosus (PDA), Arterial Venous Fistula (AVF), Arterial Venous Malformation (AVM), or a Para-Valvular Leak (PVL).

The present invention has been described above with reference to specific embodiments. However, other embodiments than the above described are equally possible within the scope of the invention. The different features and steps of the invention may be combined in other combinations than those described. The scope of the invention is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A medical implantable occlusion device comprising a braiding of at least one thread, said braiding having an unloaded relaxed state and a stretched state and comprising, in said unloaded relaxed state,
    an expanded diameter portion,
    a tubular member extending along a longitudinal axis, said tubular member having a distal region towards said expanded diameter portion and an opposite proximal region, wherein a distal end of said distal region forms a distal rim at a distal end of the tubular member and a proximal end of said proximal region forms a proximal rim at a proximal end of the tubular member, and wherein said tubular member tapers continuously inwardly from said proximal rim to said distal rim and towards said longitudinal axis, and,
    a stem having a first end directly connected to said expanded diameter portion and a second end directly connected to said distal region, wherein said stem in said relaxed state is partly sunk into said tubular member beneath said distal rim whereby said second end of said stem is displaced from said distal rim by a first offset along said longitudinal axis, wherein said proximal region comprises a connecting member for a delivery device, wherein ends of said at least one thread are fixed to said connecting member, and wherein said expanded diameter portion comprises returning loops of said at least one thread whereby opposite ends of said at least one thread forming said expanded diameter portion are fixed to said connecting member being the connection point for said opposite ends.

2. Occlusion device according to claim 1, wherein the distance between said distal rim and said expanded diameter portion is substantially smaller than the length of said stem.

3. Occlusion device according to claim 1, wherein said stem is pivotable with respect to said tubular member around said second end of said stem.

4. Occlusion device according to claim 1, wherein said stem is concentric with respect to said tubular member.

5. Occlusion device according to claim 1, wherein said second end of said stem is connected to a distal surface of said distal region, wherein said distal surface is sunk into said tubular member beneath said distal rim.

6. Occlusion device according to claim 5, wherein said distal surface is confined to a region of said braiding between said stem and said distal rim and having a diameter substantially equal to the diameter of said distal rim.

7. Occlusion device according to claim 1, wherein said tubular member is tapered towards said expanded diameter portion.

8. Occlusion device according to claim 1, wherein said tubular member and said expanded diameter portion are elastically stretchable relative each other along said longitudinal axis such that a first offset there between is variable in said relaxed state, such that said device is self-contracting.

9. Occlusion device according to claim 1, wherein said expanded diameter portion is a disc shaped portion, and wherein the diameter of said expanded diameter portion is larger than a largest diameter of said tubular member.

10. Occlusion device according to claim 1, wherein the diameter of said stem is substantially smaller than a diameter of said tubular member.

11. Occlusion device according to claim 1, wherein said distal rim is located in a plane substantially orthogonal to said longitudinal axis.

12. Occlusion device according to claim 1, wherein a distal end of said connecting member is offset towards said expanded diameter portion relative said proximal rim.

13. Occlusion device according to claim 1, comprising a proximal surface between said proximal rim and said connecting member, wherein said proximal surface is sunk into said tubular member.

14. Occlusion device according to claim 1, wherein said connecting member is at least partly spherical.

15. A medical implantable occlusion device comprising a braiding of at least one thread, said braiding having an unloaded relaxed state and a stretched state and comprising an expanded diameter portion,
a tubular member extending along a longitudinal axis, said tubular member having a distal region towards said expanded diameter portion and an opposite proximal region, wherein said distal region comprises a distal rim opposing said expanded diameter portion, wherein said proximal region comprises a proximal rim at a proximal end of the proximal region, and wherein said tubular member tapers continuously inwardly from said proximal rim to said distal rim and towards said longitudinal axis, and
a stem having a first end connected to said expanded diameter portion and a second end connected to said distal region, wherein said stem in said relaxed state is partly offset towards said proximal region relative said distal rim and along said longitudinal axis, wherein said proximal region comprises a connecting member for a delivery device, wherein opposite ends of said at least one thread are attached to said connecting member.

16. Occlusion device according to claim 15, wherein said distal rim is located in a plane substantially orthogonal to said longitudinal axis.

17. Occlusion device according to claim 15, wherein a distal end of said connecting member is offset towards said expanded diameter portion relative said proximal rim.

18. Occlusion device according to claim 17, comprising a proximal surface between said proximal rim and said connecting member, wherein said proximal surface is sunk into said tubular member.

19. Occlusion device according to claim 18, wherein said connecting member is at least partly spherical.

\* \* \* \* \*